US008678992B2

(12) United States Patent
Hong

(10) Patent No.: US 8,678,992 B2

(45) Date of Patent: Mar. 25, 2014

(54) METHOD OF COLLECTING SEMEN FROM LAB ANIMALS AND ARTIFICIAL INSEMINATION METHOD THEREOF

(75) Inventor: Jeong Sup Hong, Seoul (KR)

(73) Assignee: Korea Testing and Research Institute, Seoul (KR)

( * ) Notice: Subject to any disclaimer, the term of this patent is extended or adjusted under 35 U.S.C. 154(b) by 0 days.

(21) Appl. No.: 13/001,981

(22) PCT Filed: Oct. 16, 2009

(86) PCT No.: PCT/KR2009/005988

§ 371 (c)(1), (2), (4) Date: Jan. 6, 2011

(87) PCT Pub. No.: WO2010/134672

PCT Pub. Date: Nov. 25, 2010

(65) Prior Publication Data

US 2012/0059215 A1 Mar. 8, 2012

(30) Foreign Application Priority Data

May 22, 2009 (KR) ........................ 10-2009-0045066
Oct. 6, 2009 (KR) ........................ 10-2009-0094688

(51) Int. Cl.
*A61B 17/43* (2006.01)
*A61D 7/00* (2006.01)

(52) U.S. Cl.
USPC ............. 600/35; 435/352; 435/353; 435/354; 435/325; 435/350; 604/906; 128/897; 128/898

(58) Field of Classification Search
USPC ............ 600/35; 435/352, 353, 354, 325, 350; 604/906; 128/89
See application file for complete search history.

(56) References Cited

U.S. PATENT DOCUMENTS

| | | | | |
|---|---|---|---|---|
| 6,271,436 | B1 * | 8/2001 | Piedrahita et al. | 800/21 |
| 6,593,139 | B1 * | 7/2003 | Yanagimachi et al. | 435/375 |
| 2007/0061910 | A1 | 3/2007 | Han et al. | |
| 2007/0136830 | A1 | 6/2007 | Hammer et al. | |

FOREIGN PATENT DOCUMENTS

| | | | |
|---|---|---|---|
| JP | 2009-005651 | A | 1/2009 |
| KR | 10-0829080 | B1 | 5/2008 |
| KR | 10-2009-0013543 | A | 2/2009 |

OTHER PUBLICATIONS

Nixon B, Jones RC, Clarke HG, Holland MK. Rabbit epididymal secretory proteins. II. Immunolocalization and sperm association of REP38. Biol Reprod. Jul. 2002;67(1):140-146.*

Cho et al., English translation of Pat. No. KR100829080, May 19, 2008, Republic of Korea (management department: agriculture Promotion Center).*

(Continued)

*Primary Examiner* — Christine Matthews
*Assistant Examiner* — Sunita Reddy
(74) *Attorney, Agent, or Firm* — Edwards Wildman Palmer LLP

(57) ABSTRACT

The present invention relates to a method of collecting semen from the epididymis or the testis of a lab animal and an artificial insemination method thereof. The present invention relates to a new applicable method in the animal production field using artificial insemination. Since the present invention solves the problems of the conventional method of artificial insemination of lab animals, it is excellent in terms of the pregnancy rate and productivity; is time-efficient; and is superior in economic and industrial respects by preventing a huge economic loss due to the costs for maintaining the mass breeding of animals.

20 Claims, 2 Drawing Sheets

(56) References Cited

OTHER PUBLICATIONS

Figure 1:
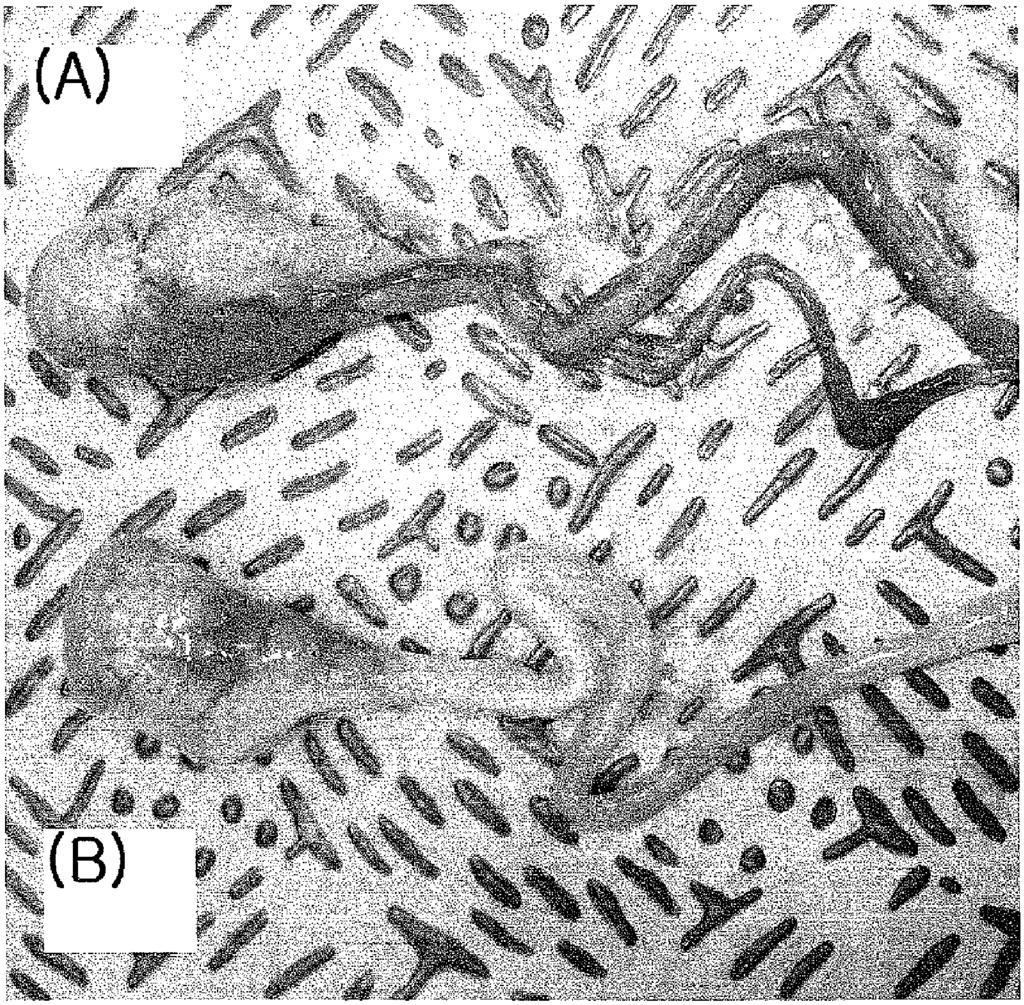

Lee et al., English Translation of Pub. No. KR 1020090013543, Feb. 5, 2009, Konkuk University Industrial Cooperation Corp.*

Office Action for Application No. GB1101405.7, dated Jul. 16, 2012.

International Search Report for PCT/KR2009/005988, mailed Jul. 6, 2010.

* cited by examiner

METHOD OF COLLECTING SEMEN FROM LAB ANIMALS AND ARTIFICIAL INSEMINATION METHOD THEREOF

This application is the U.S. national phase, pursuant to 37 U.S.C §371, of PCT International Application PCT/KR2009/005988, filed Oct. 16, 2009, which claims priority to Korean Patent Application Nos. 10-2009-0045066, filed May 22, 2009 and 10-2009-0094688 filed Oct. 6, 2009. The entire contents of the aforementioned patent applications are incorporated herein by this reference.

TECHNICAL FIELD

The present invention relates to a method of collecting semen from the epididymis or the testis of a lab animal and an artificial insemination method thereof.

BACKGROUND ART

Rabbits, which are an important animal species used as lab animals, are mainly used for the purpose of research or authorization in various fields such as pharmacology, immunology, hematology, pathology, endocrinology, etc. In the reproductive toxicological respect, rabbits are used as a useful animal species for detecting the teratogenicity of drugs. For a female rabbit, a natural ovulation does not occur, but an ovulation is induced by mating stimulation of a male or hormone or electrical stimulation, and thus according to necessity, the mating time and the number of the mating animals can be controlled. In addition, since the size of the fetus of the female rabbit is comparatively larger than that of a rat or mouse, the female rabbit has an advantage that more exact observations can be made at the time of the morphological detection of the fetus (Gibson, J P, Staples, R E and Newberne, J W (1966): Use of rabbit in teratogenecity studies. Toxicol and Appl Pharmacol, 9:398-408). Because of these various advantages, the guidelines for toxicity tests of the U.S. Food and Drug Administration (FDA), Organization for Economic Cooperation and Development (OECD) and the National Institute of Safety Research also prescribe that rabbits must be used for the evaluation of the teratogenicity using non-rodents.

The teratogenicity test using rabbits requires numerous pregnant animals for a short time. There are two methods currently used for the above purpose: a natural mating method in which the female and male rabbits directly mate; and an artificial insemination method in which the semen ejaculated outside according to the natural mounting acts of the male rabbits is collected using an artificial vagina and the collected semen is injected into the female rabbit.

However, the natural mating method has the shortcoming that it needs much time and effort and requires numerous male animals. The artificial insemination of rabbits using the artificial vagina method has the problem that the time required for semen collection is very irregular according to the condition of the male rabbit; the semen ejaculation and collection rates are very low; and the failure probability is high due to impurities such as urine. In addition, since the artificial insemination method requires a great quantity of unnecessary male rabbits for inducing the mounting act, it is very inefficient in terms of facilities maintenance and breeding space utilization.

Meanwhile, the collection of semen is first required for the artificial insemination of animals. For the semen collection causing ejaculation by artificially stimulating the ejaculation center, various methods are used according to the species of the animals, for example, a massage method, an electrical stimulation method, a hydraulic pressure method, an artificial vagina method, etc.

The massage method, which is mainly used for turkeys or cocks, is to, in the case of cocks, turn their heads upside down and, after a massage between the pubis and the carina, push the basal part of the degenerated copulatory organ, thereby collecting the leaked semen.

The electrical stimulation method, which is used for pigs, cows, sheep, dogs, etc., is to apply electrical stimulation to the sacrum part to excite the ejaculation center, thereby collecting semen.

The hydraulic pressure method, which is mainly used in pigs, is to stimulate the sexual appetite of pigs and mount the dummy and apply pressure by hand at the moment when the penis comes out, thereby having the pigs ejaculate.

The artificial vagina method, which is mainly used for cows, horses, sheep and rabbits and is partially used for pigs, is to have ejaculation occur within the artificial vagina by using an artificially-made vagina which has temperature and pressure conditions similar to the reproductive organs of animals.

Meanwhile, since minute blood vessels are complicatedly entangled within the vas deferens and the epididymis, if the semen is collected by inserting a catheter directly into the above vas deferens and epididymis, there is a problem that the semen and the blood are mixed and thus pure semen cannot be obtained.

Accordingly, the inventors of the present invention studied a new artificial insemination method and semen collection method which will improve the problems of the conventional method of artificial insemination of lab animals, thereby completing the present invention regarding a method of collecting semen from the epididymis or the testis of a lab animal and an artificial insemination method using it, which is excellent in terms of the pregnancy rate and productivity; is time-efficient; and is superior in economic and industrial respects by preventing a huge economic loss due to the costs for maintaining the mass breeding of animals.

DISCLOSURE OF INVENTION

Technical Problem

The object of the present invention is to provide a method of collecting semen from the epididymis or the testis of a lab animal and an artificial insemination method using it, which is excellent in terms of the pregnancy rate and productivity; is time-efficient; and is superior in economic and industrial respects by preventing a huge economic loss due to the costs for maintaining the mass breeding of animals.

Technical Solution

In order to achieve the above object, the present invention provides a method of removing external blood vessels on the vas deferens of a lab animal and collecting semen from the vas deferens from which the above blood vessels are removed.

In addition, the present invention provides a method of removing the testis artery and vein existing outside the vas deferens of the lab animal and collecting semen from the vas deferens from which the testis artery and vein are removed.

Further, the present invention provides a method of injecting a solvent to a membrane existing between the vas deferens and the testis artery and vein, and thereafter collecting semen from the vas deferens from which the testis artery and vein are removed. It is preferable that the solvent is a saline solution.

Furthermore, the present invention provides a method of removing the blood of the blood vessels outside the vas deferens of the lab animal and thereafter collecting semen from the vas deferens from which the above blood is removed.

In addition, the present invention provides a method removing the blood of the testis artery and vein existing outside the vas deferens of the lab animal and thereafter collecting semen from the testis artery and vein from which the above blood is removed.

Further, the present invention provides a method of injecting a solvent to the testis artery and vein existing outside the vas deferens of the lab animal, flushing the blood to remove it and thereafter collecting semen from the testis artery and vein from which the blood is removed. It is preferable that the solvent is a saline solution.

In addition, the present invention provides a method of removing the blood from the abdominal aorta or the vena cava of the lab animal by cutting the abdominal aorta or the vena cava and thereafter collecting semen from the vas deferens.

Further, the present invention provides a method of removing the external blood vessels on the epididymis of the lab animal and thereafter collecting semen from the epididymis from which the above blood vessels are removed.

In addition, the present invention provides a method of removing the external blood vessels on the epididymis of the lab animal and thereafter cutting the epididymis from which the above blood vessels are removed, and collecting semen.

Further, in the method of collecting semen according to the present invention, it is preferable to remove the blood or the blood vessels while maintaining a temperature of 30~45° C. and collect semen. It is preferable to maintain the temperature when removing the above blood, at 30~45° C. Since the temperature has a great influence on the activity of the sperm existing in the vas deferens and the epididyms, the temperatures of all the parts used in removing the blood such as an injection needle, a physiological saline solution, etc. were heated to a temperature within the range of 37~40° C. similar to the body temperature of the rabbit.

In addition, the method of collecting semen according to the present invention is preferable as a method of collecting semen of rabbits, mice, rats, dogs or guinea pigs.

Further, the present invention provides an artificial insemination method of removing the external blood vessels on the vas deferens of the lab animal and thereafter collecting semen from the vas deferens in which the blood vessels are removed, and injecting the collected semen into the female. More specifically, the present invention provides the artificial insemination method of injecting a solvent into a membrane existing between the vas deferens and the testis artery and vein and separating the vas deferens from the testis artery and vein to remove the testis artery vein, and thereafter collecting semen from the vas deferens in which the above testis artery and vein are removed, and injecting the collected semen to the female. It is preferable that the solvent is a saline solution.

Further, the present invention provides an artificial insemination method of removing the external blood vessels on the vas deferens of the lab animal and thereafter collecting semen from the vas deferens from which the blood vessels are removed, and injecting the collected semen into the female. More specifically, the present invention provides the artificial insemination method of injecting a solvent into a membrane existing between the vas deferens and the testis artery and vein and separating the vas deferens from the testis artery and vein to remove the testis artery vein, and thereafter collecting semen from the vas deferens from which the above testis artery and vein are removed, and injecting the collected semen to the female. It is preferable that the solvent is a saline solution.

In addition, the present invention provides the artificial insemination method of removing the blood from the external blood vessels on the vas deferens of the lab animal and thereafter collecting semen from the vas deferens from which the above blood is removed, and injecting the collected semen into the female. It is preferable that the above blood vessels are the testis artery and vein. More specifically, the present invention provides the artificial insemination method of injecting a solvent into the testis artery and vein existing outside the vas deferens of the lab animal, and thereafter collecting semen from the vas deferens from which the blood is removed, and injecting the collected semen into the female. It is preferable that the above solvent is a saline solution. In addition, it is preferable to dilute the collected semen and inject it into the female.

Further, the present invention provides the artificial insemination method of removing the blood from the abdominal aorta or the vena cava of the lab animal by cutting the abdominal aorta or the vena cava, and thereafter collecting semen from the vas deferens, and injecting the collected semen into the female.

Furthermore, the present invention provides the artificial insemination method of removing the external blood vessels on the epididymis of the lab animal and thereafter collecting semen from the epididymis from which the above blood vessels are removed, and injecting the collected semen into the female. It is preferable that the above blood vessels are the testis artery and vein. More specifically, the present invention provides the artificial insemination method of removing the external blood vessels on the epididymis of the lab animal and thereafter cutting the epididymis from which the blood vessels are removed, to collect semen, and injecting the collected semen into the female. It is preferable that the above solvent is a saline solution. In addition, it is preferable to dilute the collected semen and inject it into the female animal.

In addition, in the artificial insemination method of the present invention, it is preferable to remove the blood or the blood vessels while maintaining a temperature of 30~45° C., and collect semen.

Further, the artificial insemination method of the present invention is preferable as the artificial insemination method for rabbits, mice, rats, dogs or guinea pigs.

Advantageous Effects

The present invention can provide a method of directly collecting semen from the epididymis or testis of a lab animal and an artificial insemination method using it, which is excellent in terms of the pregnancy rate and productivity; is time-efficient; and is superior in economic and industrial respects by preventing a huge economic loss due to the costs for maintaining the mass breeding of animals.

BRIEF DESCRIPTION OF DRAWINGS (A) of FIG. 1 shows the vas deferens before the external blood vessels are removed, and (B) shows the vas deferens from which the external blood vessels are removed.

Figure 2:
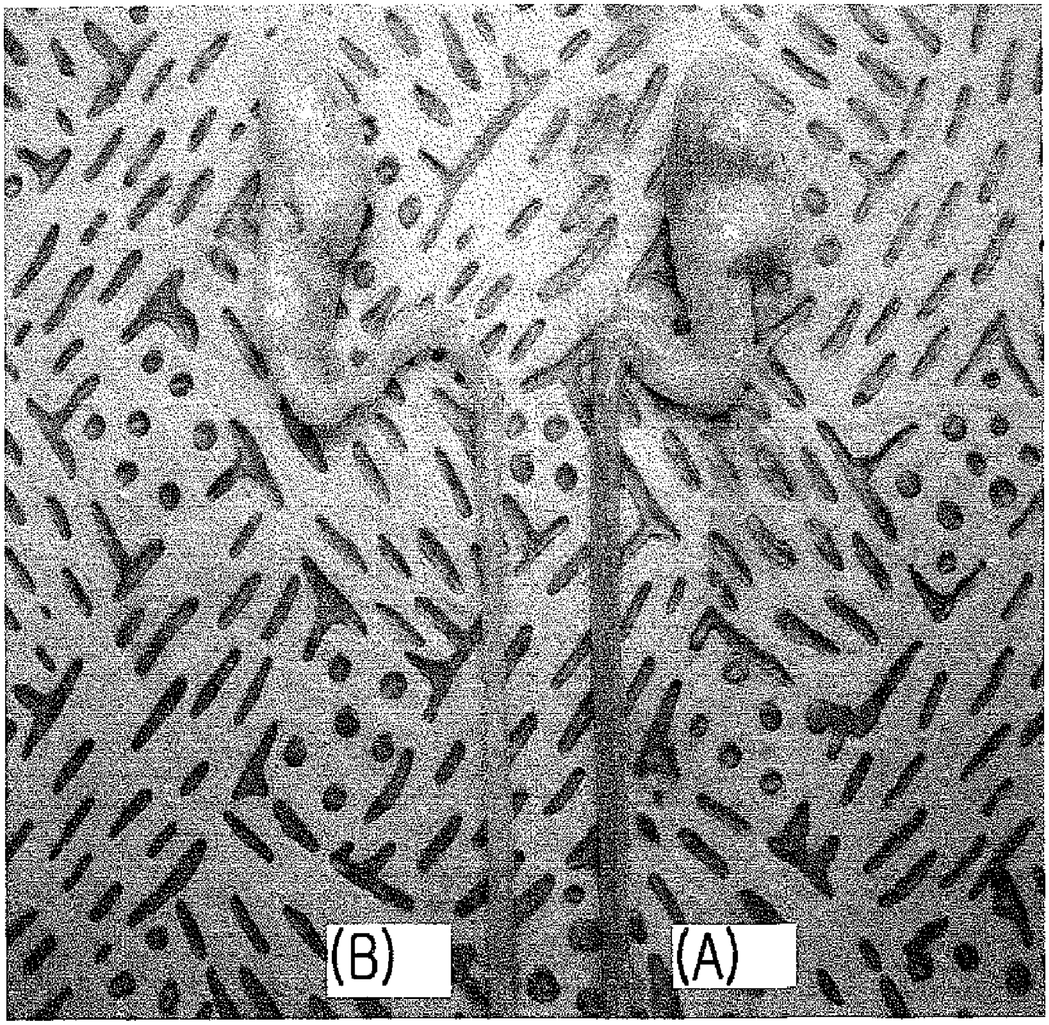

(A) of FIG. 2 shows the epididymis and the vas deferens before the blood of the external blood vessels is removed, and (B) shows the epididymis and the vas deferens from which the blood of the external blood vessels is removed.

BEST MODE FOR CARRYING OUT THE INVENTION

Hereinafter, preferred working examples are described for the purpose of making the present invention understood. However, the following working examples are provided merely for making the present invention more easily understood, but the scope of the present invention is not limited to the following working examples.

Example 1

Directly Collecting Semen From the Vas Deferens of a Rabbit (1) While the temperature was maintained at 30-45° C., an injection needle was penetrated into a membrane existing between the vas deferens outside wall and the vas deferens artery and vein of the male rabbit, and thereafter the physiological saline solution was injected to separate the vas deferens from the vas deferens artery and vein, and thereby the blood vessels were removed. A catheter was inserted into the vas deferens from which the above blood vessels were removed, and semen was collected through the perfusion of the physiological saline solution.

(2) In a different way, while the temperature was maintained at 30-45° C., an injection needle was penetrated into the vas deferens artery and vein located in the outside wall of the vas deferens of a male rabbit and thereafter the blood was flushed through the perfusion of the physiological saline solution. A catheter was inserted into the vas deferens from which the above blood was removed, and semen was collected through the perfusion of the physiological saline solution.

(3) In a different way, while the temperature was maintained at 30-45° C., the abdominal aorta or the vena cava of a male rabbit was cut and thereafter the blood was removed. A catheter was inserted into the vas deferens from which the above blood was removed, and semen was collected through the perfusion of the physiological saline solution.

Example 2

Directly Collecting Semen from the Epididymis of a Rabbit

While the temperature was maintained at 30-45° C., the blood vessels of the epididymis of the male rabbit were removed and the above epididymis from which the blood vessels were removed was cut and thereby semen was collected.

Through above ways of example 1 or example 2, 20 ml of semen for each individual was collected. Through the above ways, strong sperm of a high purity from which the sperm and the saline solution are mixed can be obtained.

Comparative Example 1

Collecting Semen of a Rabbit by an Artificial Insemination Method

An artificial vagina was completely assembled by filling water between a rubber tube of its inside and a plastic tube of its outside. Thereafter, until the water temperature within the artificial vagina became 45~50° C., the artificial vagina was fully floated in a thermostatic tank of 50° C.

Two male rabbits were put in a rearing box of which the upper part was open. When they started their mating behavior, the artificial vagina floating in the thermostatic tank was taken out, and on the bottom part thereof a semen collection tube was fixed, and then it was put between the rear legs of the male rabbits displaying the mating behavior, and semen was collected. Through this way, 0.5 ml of semen was collected. This was 1/40 of the volume of above example 1.

Experimental Example 1

Comparison of Semen Properties According to the Semen Collection Method

The sperm in example 1 or example 2 and comparative example 1 were compared and analyzed using a sperm analyzer (Hamilton-thron, U.S.A.) for a comparison of the sperm motility, the sperm number (concentration), and other morphological abnormalities. The results are indicated in Table 1.

TABLE 1

| | Comparative example 1 | example |
|---|---|---|
| Comparison of sperm motility | | |
| Sperm motility | 80% or more | 80% or more |
| Comparison of sperm morphology | | |
| Normal sperm | 3/100 | 2/100 |
| No head | 1 | 1 |
| Double head | — | — |
| No tail | 2 | 1 |
| Double tail | — | — |
| Hooked tail | — | — |
| Abnormality (%) | 3 (%) | 2 (%) |

As shown in Table 1, the working example and the comparative example showed an active sperm motility of 80% or more. With regard to the sperm morphology, the working example and the comparative example did not show a great difference in the number of the normal sperm. The working example has a lower abnormality (%) than the comparative example.

Experimental Example 2

Artificial Insemination Method Using the Semen Collected from the Epididymis or the Testis of Rabbits Using an injection tube, the semen of example 1 or example 2 and comparative example 1 was injected, with or without being diluted in the physiological saline solution, respectively into the left and right wombs of female rabbits (20 heads) of 3.5 kg or more. After termination of the artificial insemination, for the super ovulation induction, hCG (10 iu/KG/B.W.Rabbit) was injected into the ear vein of rabbits. The artificial insemination date was set as day 0 of pregnancy, and the caesarean section of the pregnant rabbits was performed 28 days after pregnancy to observe fertility and implantation rate (number), live fetuses, placenta and fetus weights, sex rate, external abnormality, skeletal and visceral abnormality, etc. The result was indicated in Table 2.

TABLE 2

| | Comparative example 1 | Example |
|---|---|---|
| Fertility rate (%) | 18/20 (90.0%) | 20/20 (100.0%) |
| Implantation rate (%) | 135/167 (80.3%) | 153/182 (84.9%) |
| Live fetuses/Maternal | 123/15 | 146/18 |

TABLE 2-continued

| | Comparative example 1 | Example |
|---|---|---|
| rabbit | (Avg = 8.3 fetuses) | (Avg = 8.1 fetuses) |
| Placenta weights | 4.84 g | 5.13 g |
| Body weight | 37.07 g | 36.84 g |
| Sex rate (female:male) | 1:1.12 | 1:0.90 |

As a result of performing the caesarean section 28 days after pregnancy, it was confirmed that 20 maternal heads (100%) of 20 female rabbits were finally pregnant (including initial abortion). The implantation rate was observed as 84.9% on average. With regard to the average number of live fetuses per maternal rabbit, 146 heads (8.1 heads/average number of live fetuses per maternal rabbit) of fetuses were confirmed from 18 heads of maternal rabbits except for initially aborted individuals. With regard to the sex rate of fetuses, the female and male rate was calculated as 1:0.91. As a result of measuring the placenta and fetus weights, the average weight of placentas was 5.13 g and the average weight of fetuses was 36.84 g. As a result of observing the external abnormality of placentas, no special abnormal expression was observed.

In addition, in the case of the artificial insemination by the artificial vagina method, an average of 4~5 hours or more was taken from the male semen collection to the artificial insemination termination. On the other hand, in the case of the present invention, all work was completed within 30 minutes, and regardless of the state and condition of the animals, the time and period of the artificial insemination could be arbitrarily controlled.

INDUSTRIAL APPLICABILITY

As reviewed above, the method of directly collecting semen from the epididymis or the testis of a lab animal and the artificial insemination method using it, are excellent in terms of the pregnancy rate and productivity and are time-efficient and superior in economic and industrial respects by preventing a huge economic loss due to the costs for maintaining the mass breeding of animals.

The invention claimed is:

1. A method of collecting semen, comprising the steps of:

(a) injecting a solvent to a membrane existing between the vas deferens of a male lab animal and external blood vessels on the vas deferens to separate the external blood vessels from the vas deferens; and (b) collecting semen from the vas deferens which had its external blood vessels separated in step (a).

2. The method of collecting semen as claimed in claim 1, wherein the solvent is a saline solution.

3. The method of collecting semen as claimed in claim 1, wherein steps (a) and (b) occur at 30-45° C.

4. An artificial insemination method, comprising injecting the semen collected by the method of claim 3 into the reproductive tract of a female animal.

5. The artificial insemination method as claimed in claim 4, wherein the semen is first diluted and then injected into the reproductive tract of the female animal.

6. The method of collecting semen as claimed in claim 1, wherein the male lab animal is selected from the group consisting of a rabbit, a mouse, a rat, a dog, and a guinea pig.

7. An artificial insemination method, comprising injecting the semen collected by the method of claim 6 into the reproductive tract of a female animal.

8. The artificial insemination method as claimed in claim 7, wherein the semen is first diluted and then injected into the reproductive tract of the female animal.

9. An artificial insemination method, comprising injecting the semen collected by the method of claim 1 into the reproductive tract of a female animal.

10. The artificial insemination method as claimed in claim 9, wherein the semen is first diluted and then injected into the reproductive tract of the female animal.

11. A method of collecting semen, comprising the steps of:

(a) injecting a solvent into external blood vessels on the vas deferens of a male lab animal to flush blood inside the external blood vessels and removing the external blood vessels from the vas deferens; and (b) collecting semen from the vas deferens which had its external blood vessels removed in step (a).

12. The method of collecting semen as claimed in claim 11, wherein the solvent is a saline solution.

13. An artificial insemination method, comprising injecting the semen collected by the method of claim 11 into the reproductive tract of a female animal.

14. The artificial insemination method as claimed in claim 13, wherein the male lab animal is selected from the group consisting of a rabbit, a mouse, a rat, a dog, and a guinea pig.

15. The artificial insemination method as claimed in claim 14, wherein the semen is first diluted and then injected into the reproductive tract of the female lab animal.

16. The artificial insemination method as claimed in claim 15, wherein steps (a) and (b) occur at 30-45° C.

17. A method of collecting semen, comprising the steps of:

(a) injecting a solvent into a membrane existing between the epididymis of a male lab animal and external blood vessels on the epididymis to separate the external blood vessels from the epididymis; and (b) collecting semen from the epididymis which had its external blood vessels separated in step (a).

18. The method of collecting semen as claimed in claim 17, wherein the method further comprises a step of cutting the epididymis between step (a) and step (b).

19. An artificial insemination method, comprising injecting the semen collected by the method of claim 10 into the reproductive tract of a female animal selected from the group consisting of a rabbit, a mouse, a rat, a dog, and a guinea pig.

20. The artificial insemination method as claimed in claim 19, wherein the semen is first diluted and then injected into the reproductive tract of the female animal and wherein steps (a) and (b) occur at 30-45° C.

* * * * *